US012778652B2

(12) United States Patent
Hänggi et al.

(10) Patent No.: US 12,778,652 B2
(45) Date of Patent: Nov. 3, 2026

(54) ELECTRONIC DENTAL TORQUE WRENCH

(71) Applicant: Institut Straumann AG, Basel (CH)

(72) Inventors: Beat Hänggi, Basel (CH); Steve Béguin, Nenzlingen (CH)

(73) Assignee: INSTITUT STRAUMANN AG, Basel (CH)

(*) Notice: Subject to any disclaimer, the term of this patent is extended or adjusted under 35 U.S.C. 154(b) by 0 days.

(21) Appl. No.: 19/254,394

(22) Filed: Jun. 30, 2025

(65) Prior Publication Data

US 2026/0096839 A1 Apr. 9, 2026

(30) Foreign Application Priority Data

Jun. 28, 2024 (WO) ................. PCT/EP2024/068404

(51) Int. Cl.
*A61B 17/88* (2006.01)
*A61B 90/00* (2016.01)

(52) U.S. Cl.
CPC .......... *A61B 17/8875* (2013.01); *A61B 90/03* (2016.02); *A61B 90/06* (2016.02); *A61B 2090/031* (2016.02); *A61B 2090/066* (2016.02)

(58) Field of Classification Search
CPC ..... A61B 17/88; A61B 17/8875; A61B 90/00; A61B 90/03; A61B 90/06; B25B 23/14; B25B 23/1425; B25B 23/46; B25B 23/462
See application file for complete search history.

(56) References Cited

U.S. PATENT DOCUMENTS

| | | | | |
|---|---|---|---|---|
| 7,194,940 | B2 * | 3/2007 | Hsieh | B25B 13/08 81/479 |
| 7,597,032 | B2 * | 10/2009 | Baumgartner | A61C 8/0089 81/60 |
| 10,046,445 | B2 * | 8/2018 | Gauthier | A61B 17/8875 |
| 12,070,372 | B2 * | 8/2024 | Brechbühl | A61C 8/0089 |

FOREIGN PATENT DOCUMENTS

| | | | |
|---|---|---|---|
| DE | 20 2004 014195 | U1 | 11/2004 |
| DE | 202004012225 | U1 | 12/2004 |
| DE | 202005012623 | U1 | 12/2005 |
| DE | 202007012866 | U1 | 1/2008 |
| WO | 2020/182973 | A1 | 9/2020 |

OTHER PUBLICATIONS

Feb. 13, 2025 International Search Report issued in International Patent Application No. PCT/EP2024/068404.

* cited by examiner

*Primary Examiner* — Christopher J Beccia
(74) *Attorney, Agent, or Firm* — Oliff PLC

(57) ABSTRACT

An electronic dental torque wrench is described, including a head with a receiving opening defining a rotation axis and configured to receive a screwing instrument, a shaft defining a shaft axis and configured for applying a torque to the head, wherein the receiving opening is configured to engage with the screwing instrument upon rotation of the shaft around the rotation axis in a tightening direction, wherein the shaft includes a force sensor including one or more force-sensitive resistors and configured to sense the force on the shaft generated upon rotation of the shaft around the rotation axis in a tightening direction, wherein the one or more force-sensitive resistors are arranged at one or more sensor surfaces which are substantially perpendicular to the tightening direction.

20 Claims, 13 Drawing Sheets

ELECTRONIC DENTAL TORQUE WRENCH

FIELD OF THE INVENTION

The present invention relates to an electronic torque wrench for medical technology, specifically suitable for dentistry, an electronic torque wrench system comprising an electronic torque wrench and a method of monitoring an electronic torque wrench.

BACKGROUND OF THE INVENTION

In dental implantology, it is known to insert implants into the jawbone and to fasten connection elements, such as abutments, to the implants, on which connection elements the superstructure is then placed, for example a crown or bridge. In order to screw in the implant or the connection element, a screwing instrument can be applied in a form-fitting manner and rotated via a torque wrench.

A torque wrench with a ratchet function for use in dental implantology is for example described in WO 2020/182973 A1. The torque wrench comprises a head region with a receiving opening, a bending-resistant shaft region adjoining the head region, a support formed on the shaft region, and an actuating lever including an elastically bendable portion and a handle. The receiving opening receives a screwing instrument and defines an axis of rotation. The actuating lever, in resting position, is spaced apart from the in the circumferential direction to the axis of rotation. If a screwing instrument is inserted into the opening, the actuating lever transmits a torque. The torque wrench has an indicator region, which the exerted torque can be read as a result of the deflection of the actuating lever. When a reference force is reached, the bending portion comes into contact with the support. When a force is applied, the bending portion can be in the tightening direction and the torque can be read in the region.

A torque wrench for medical technology is for example also described in DE 20 2004 014 195 U1, said torque wrench comprising a frontmost head region, an adjoining neck region which is followed by a shaft region, and a handle region. The head region, the neck region, the shaft region and the handle region extend in one plane. The torque wrench furthermore comprises a receptacle opening which is provided in the head region, is surrounded by a bezel, and possesses a center through which an axis extends as to be perpendicular to the plane. The receptacle opening serves for inserting a driver instrument in the extent of the axis. The torque wrench furthermore comprises a ratchet segment of limited mobility which is disposed on the periphery of the receptacle opening, the front part of said ratchet segment pointing toward the receptacle opening. The front part is configured, when the torque wrench is activated in the screw-in mode, for engaging in an entraining manner with an external contour present on the head of the driver instrument, and when the torque wrench is activated in the reverse direction, thus in the ratchet mode, for releasing the entraining engagement with the external contour present on the head of the driver instrument. The torque wrench furthermore comprises a flexurally stiff base shank which from the neck region extends along the shaft region. A ratchet spring extends from the ratchet segment into the neck region, wherein the ratchet Segment and the ratchet spring form an integral ratchet. Long thin slots which permit the ratchet to deflect, counter to the force of the ratchet spring, in the plane are configured on both sides of the ratchet. The ratchet is furthermore formed integrally from the neck region.

SUMMARY OF THE INVENTION

While manually installing a dental implant by a dental practitioner using a torque wrench, it is desired that the torque is applied in a precise and accurate manner. Thereby, it is desired that the dental practitioner is provided with a simple and clear indication of the applied torque such that the dental practitioner may adjust the force during installation of the dental implant.

It is therefore an object of the invention to provide a torque wrench for dental implantology and a method of monitoring a torque wrench which at least partially improve the prior art and avoid at least part of the disadvantages of the prior art.

According to the present invention, this object is achieved by the features of the independent claims. In addition, further advantageous embodiments follow from the dependent claims and the description as well as the figures.

According to an aspect of the invention, this object is particularly achieved by an electronic dental torque wrench, comprising a head with a receiving opening defining a rotation axis and configured to receive a screwing instrument, a shaft defining a shaft axis and configured for applying a torque to the head, wherein the receiving opening is configured to engage with the screwing instrument upon rotation of the shaft around the rotation axis in a tightening direction, wherein the shaft comprises a force sensor comprising one or more force-sensitive resistors and configured to sense the force on the shaft generated upon rotation of the shaft around the rotation axis in a tightening direction, wherein the one or more force-sensitive resistors are arranged at one or more sensor surfaces which are substantially perpendicular to the tightening direction.

Using the force sensor, the applied torque can therefore be determined electronically by measuring the force on the shaft generated while rotating the screwing instrument by the electronic dental torque wrench for installation of the dental implant. The force sensor provides the advantage that reliable and precise torque values can be indicated, especially compared to torque indication means using mechanical components only.

The force sensor provides the further advantage that the sensor signal generated by the force sensor can be digitized and used for display on an output device such as an external monitor. Furthermore, the digitized sensor signal may be stored and used for digital documentation of the installation process of the dental implant.

By arranging the one or more force sensors at one or more sensor surfaces substantially perpendicular to the tightening direction, the sensor signal can be improved since the forces when tightening the electronic dental torque wrench typically occur primarily in the tightening direction. Furthermore, detrimental influence on the sensing signal due to shear forces may be reduced compared to an arrangement of the one or more force sensors at a sensor surface oriented substantially perpendicular to the rotation axis.

In some embodiments, the head of the electronic dental torque wrench comprises a ratchet arranged at the receiving opening, wherein the ratchet is configured to engage with the screwing instrument upon rotation of the shaft around the rotation axis in a tightening direction and to provide a freewheel upon rotation of the shaft around the rotation axis against the tightening direction.

Due to the ratchet of the head region, free running of the inserted screwing instrument during a rotation against the tightening direction can be permitted. Screwing and/or unscrewing without repeatedly releasing the torque wrench from the screwing instrument and repeatedly mounting it on the screwing instrument can therefore be enabled, thereby facilitating practical operation of the torque wrench.

Preferably, the force sensor comprises a plurality of force-sensitive resistors, preferably connected in a Wheatstone bridge circuit.

By using force-sensitive resistors for the force sensor, the force sensor can be kept small while enabling a reliable sensing of the force on the shaft. The one or more of the force-sensitive resistors may be strain-sensitive resistors, in particular, made of strain gauges. Miniaturization of the force sensor is especially advantageous for the use in dental implantology where the available space within and at the vicinity of the oral cavity is limited. A Wheatstone bridge circuit thereby represents a simple and precise measurement circuit for force sensing using force-sensitive resistors.

In some embodiments, the shaft comprises a clearance which is open in a direction parallel to the rotation axis and closed in and against the tightening direction by a first shaft wall and a second shaft wall each having an outer surface and an inner surface, wherein the one or more sensor surfaces are arranged at the shaft walls.

Due to the clearance, the local strain may be increased at the shaft walls when applying a torque by the electronic dental torque wrench. By arranging the one or more sensor surfaces at which the one or more force-sensitive resistors are arranged at the shaft walls, the sensing signal and sensitivity of the force sensor can therefore be increased.

The clearance may further provide additional space for arranging the force sensor at the shaft without increasing the dimensions of the electronic dental torque wrench.

In some embodiments, the one or more sensor surfaces are arranged at a front end of the clearance with respect to the head of the electronic dental torque wrench.

The clearance may therefore comprise a front end and a rear end with the front end being closer to the head than the rear end.

The increase of the local strain due to the clearance may especially be significant at the front end and/or the rear end of the clearance where the first and second shaft walls join the solid or, respectively, filled portion of the shaft.

In some embodiments, the one or more sensor surfaces are arranged at the outer surface of the first shaft wall and/or the second shaft wall.

By arranging the one or more sensor surfaces at which the one or more force-sensitive resistors are arranged at the outer surface of the first shaft wall and/or second shaft wall, access to the force sensor can be facilitated, which may be advantageous for repairing the measurement circuit or replacement of components such as the force-sensitive resistors.

In some embodiments, the one or more sensor surfaces are arranged at the inner surface of the first shaft wall and/or the second shaft wall.

By arranging the one or more sensor surfaces at which the one or more force-sensitive resistors are arranged at the inner surface of the first and/or second shaft wall, protection of the force sensor against detrimental external influences, such as the temperature from the hand of the dental practitioner and/or from the oral cavity of the patient, can be improved. Furthermore, the force sensor may better be protected against mechanical damage.

In some embodiments, one or more of the one or more sensor surfaces are arranged at the outer surface of the first shaft wall and/or the second shaft wall and one or more of the one or more sensor surfaces are arranged at the inner surface of the first shaft wall and/or the second shaft wall.

Thus, one or more of the one or more force-sensitive resistors may be arranged at the outer surface of the first shaft wall and/or the second shaft wall and one or more of the one or more force-sensitive resistors may be arranged at the inner surface of the first shaft wall and/or the second shaft wall.

The clearance therefore provides the advantage that a variety of possible arrangements of the one or more force-sensitive resistors at the outer and/or inner surfaces of the first and/or second shaft walls can be used for the electronic dental torque wrench, depending for example on the specific measurement purpose or design requirements. The different arrangement possibilities for the one or more force-sensitive resistors may for example be used to sense on the one hand a compressive strain and on the other hand tensile strain while operating the electronic dental torque wrench.

In some embodiments, the clearance has a shape of a slotted hole.

The clearance may therefore have an elongated shape, such that the region with higher strain may be increased. Furthermore, the available space for arranging the force-sensitive resistors at the clearance may be increased.

In some embodiments, the clearance has a shape of a borehole, having for example a circular or square shape.

In some embodiments, the shaft comprises a first recess with a first floor which is delimited by a front and a rear recess wall with respect to the shaft axis, wherein a first sensor surface of the one or more sensor surfaces is arranged at the first floor.

Therefore, one or more of the one or more force-sensitive resistors may be arranged in the first recess. By arranging one or more force-sensitive resistors in the first recess, a certain protection for the force-sensitive resistors can be provided, for example against the influence of the temperature from the hand h of the dental practitioner operating the electronic dental torque wrench and/or from the oral cavity of the patient.

In some embodiments, the first floor of the first recess at least partially coincides with the outer surface of the first shaft wall.

Thus, the first recess with one or more force-sensitive resistors may be arranged at a region of the shaft where the clearance is formed. At least a part of the outer surface of the first shaft wall may thereby form at least part of the first floor of the first recess.

In some embodiments, a front end of the clearance is axially offset with respect to the front recess wall of the first recess such that the front end of the clearance is axially positioned between the front recess wall and the rear recess wall of the first recess.

By offsetting the front end of the clearance along the shaft axis with respect to the front recess wall of the first recess such that the front end of the clearance is axially positioned between the front recess wall and the rear recess wall of the first recess, the position in the first recess where the maximal strain occurs, can be varied. Varying the position in the first recess where the maximal strain occurs may be advantageous for positioning the one or more force-sensitive resistors, depending on the design of the force-sensitive resistors and/or the design of the measurement circuit.

By arranging one or more force-sensitive resistors in the region where the maximal strain occurs, the sensing signal and the sensitivity of the force sensor can therefore be increased.

For example, the front end of the clearance may be offset with respect to the front recess wall of the first recess such that the front end of the clearance may be arranged at the axial position of the center of the first recess, such that the maximal strain occurs at the center of the first recess.

In some embodiments, the axial position of the front end of the clearance is closer to the front recess wall than to the rear recess wall of the first recess or wherein the axial position of the front end of the clearance is closer to the rear recess wall than to the front recess wall of the first recess.

The front end of the clearance may therefore be offset along the shaft axis with respect to the front recess wall of the first recess such that the maximal strain occurs in a front region of the first recess or in a rear region of the first recess.

In some embodiments, the rear recess wall f the first recess is closer to the head than a rear end of the clearance.

The rear end of the clearance may therefore extend further into a rear region of the shaft than the first recess, such that the maximal or strongly increased strain may predominantly occur around one position in the first recess.

In some embodiments, a rear end of the clearance is axially offset with respect to the rear recess wall of the first recess such that the rear end of the clearance is axially positioned between the front recess wall and the rear recess wall of the first recess.

The axial offset of the clearance may therefore apply to the front end of the clearance with respect to the front recess wall of the first recess or to the rear end of the clearance with respect to the rear recess wall of the first recess.

In some embodiments, the shaft comprises a second recess with a second floor which is delimited by a front and a rear recess wall with respect to the shaft axis, wherein a second sensor surface of the one or more sensor surfaces is arranged at the second floor.

Therefore, a first part of the force sensor may be arranged in the first recess and a second part of the force sensor may be arranged in the second recess. For example, a first Wheatstone bridge circuit may be arranged in the first recess and a second Wheatstone bridge circuit may be arranged in the second recess. The second recess may be oppositely arranged to the first recess in a mirrored fashion with respect to the shaft axis.

In some embodiments, the second floor of the second recess at least partially coincides with the outer surface of the second shaft wall.

Thus, the second recess with one or more force-sensitive resistors may be arranged at a region of the shaft where the clearance is formed. At least a part of the outer surface of the second shaft wall may thereby form at least part of the second floor of the second recess.

In particular, the features of the axial offset of the front end or rear end of the clearance with respect to the first recess, as described in one or more of the preceding paragraphs, may accordingly apply also in connection with the second recess.

In some embodiments, the shaft comprises a third recess, preferably extending along the shaft axis.

The third recess may be arranged in a plane perpendicular to the rotation axis.

The third recess may especially be used as a wire channel to guide the wires for electrical connection of the force-sensitive resistors. By arranging the wires in the third recess, protection of the wires can be provided.

In embodiments, the third recess extends from the clearance.

Due to the third recess extending from the clearance, wires running from force-sensitive resistors arranged on the first and/or second shaft wall may be guided along the shaft without protruding from the shaft.

In some embodiments, the first and/or second shaft wall comprises a notch extending perpendicular to the outer surface of the first and/or second shaft wall, wherein the notch provides a passage from the outer surface of the first and/or second shaft wall to the third recess.

Using the notch, wires running from force-sensitive resistors arranged on the outer surface of the first and/or second shaft wall may be guided to the third recess without protruding from the shaft.

In some embodiments, the head comprises a first interface connector and the shaft comprises a second interface connector interconnectable with the first interface connector such that the head and the shaft are releasably connectable by an interface formed by the first interface connector and the second interface connector.

Due to the force sensor being arranged at the shaft of the electronic dental torque wrench and the shaft being releasably connectable with the head, sterilization of the head can be performed without detrimentally affecting the force sensor and its electronic components since the head can be disconnected from the shaft prior to sterilization. Furthermore, various shafts with different designs may be used with the head, depending for example on specific user requirements.

In some embodiments, the first interface connector and the second interface connector are configured to form a form-fit and/or force-fit connection.

In some embodiments, the first interface connector and the second interface connector are configured to form a dovetail connection, a plug-socket connection, or a screw connection.

In some embodiments, the force sensor comprises one or more temperature compensation elements configured to compensate a temperature drift of a sensing signal of the force sensor.

For example, the force sensor may comprise one or more temperature compensation resistors connected in series to one or more of the force-sensitive resistors. For a force sensor comprising a Wheatstone bridge circuit for example, the output voltage may be measured at different temperatures at a calibration step of the force sensor. Using the different values of the output voltage measured at different temperatures, suitable temperature compensation resistors may be added to the Wheatstone bridge circuit in order to compensate for the temperature drift of the force-sensitive resistors.

In some embodiments, the electronic dental torque wrench comprises an accelerometer and/or a gyroscope sensor.

By providing an accelerometer and/or a gyroscope sensor, information on the orientation and/or acceleration, especially angular acceleration, during operation of the electronic dental torque wrench can be obtained. The information on the orientation and/or acceleration can be synchronized with the torque information obtained from the force sensor. Using the information collected by at least one of the accelerometer, the gyroscope sensor, or the force sensor, documentation of the surgical procedure can be improved.

In some embodiments, the accelerometer and/or the gyroscope sensor is arranged at the head, preferably at the receiving opening.

In particular, the accelerometer and/or the gyroscope sensor may be mounted at the receiving opening such that the accelerometer and/or the gyroscope sensor is arranged on the rotation axis. Using such an arrangement, sensor data may be used without extensive transformation calculation of the raw signal.

In some embodiments, the accelerometer and/or the gyroscope sensor is arranged at the shaft.

Arranging the accelerometer and/or the gyroscope sensor at the shaft provides the advantage that the accelerometer and/or the gyroscope sensor may be unaffected or less affected by a sterilization of the head.

In some embodiments, the electronic dental torque wrench comprises a positioning sleeve placeable over a portion of the electronic dental torque wrench, wherein the accelerometer and/or the gyroscope sensor is arranged on the positioning sleeve.

Therefore, the positioning sleeve with the accelerometer and/or the gyroscope sensor may be removed from the electronic dental torque wrench during sterilization of the head. The positioning sleeve may provide the further advantage that the position of the accelerometer and/or the gyroscope sensor may be varied, especially along the shaft axis.

In some embodiments, the positioning sleeve is placeable over the head.

In some embodiments, the positioning sleeve is placeable over the shaft.

Preferably, the accelerometer and gyroscope sensor are integrated in a combined acceleration-gyroscope sensor.

In some embodiments, the electronic dental torque wrench comprises a protective sleeve placeable over at least a part of the force sensor.

The protective sleeve provides the advantage that protection of the force-sensitive resistors and/or the wires of the force sensor can be improved.

The protective sleeve and/or the positioning sleeve may be made of a plastic material. The protective sleeve and/or the positioning sleeve may comprise rigid and/or flexible parts. The protective sleeve and/or the positioning sleeve may be made as a one-piece or a multi-piece component. The protective sleeve may comprise a first opening configured to receive the head therethrough and a second opening configured to receive the shaft therethrough.

In some embodiments with a positioning sleeve for the accelerometer and/or gyroscope sensor, the positioning sleeve may be configured that the positioning sleeve functions as a protective sleeve for the force-sensitive resistors.

In some embodiments, the shaft may comprise a sensor-carrying part and a gripping part which are releasably mounted together. The gripping part may separately be sterilized before or after use of the electronic dental torque wrench.

The protective sleeve may be placeable over the sensor-carrying part of the shaft and comprise a first opening configured to receive the head therethrough and a second opening configured to receive the gripping part therethrough.

In some embodiments, the protective sleeve may comprise a main body and a cap closing the main body.

In some embodiments, the shaft and/or the head comprises fourth recess. The fourth recess may be configured to engage with the protective sleeve and/or the positioning sleeve, preferably in a snap-fit fashion.

In some embodiments, the force sensor comprises a plurality of force-sensitive resistors, wherein a first group of the force-sensitive resistors is oriented perpendicular to a second group of the force-sensitive resistors.

In embodiments with only two force-sensitive resistors, one force-sensitive resistor may therefore be oriented perpendicular to the other force-sensitive resistor.

Due to the perpendicular orientation of the first group and second group of force-sensitive resistors, forces on the shaft acting in different directions may be sensed. In particular, a force on the shaft generated upon rotation of the shaft around the rotation axis in a tightening direction may not only be oriented perpendicular to the rotation axis, but also in different deviating directions, depending on e.g. how the user holds and/or moves the electronic dental torque wrench. Furthermore, rotation of the shaft around the rotation axis in a tightening direction may also generate torsion on the shaft which may also be sensed by the force sensor with suitably oriented one or more force-sensitive resistors. For example, a force-sensitive resistor oriented parallel to the rotation axis may be sensitive to torsional forces acting on the shaft.

In some embodiments, the force sensor comprises one or more secondary force-sensitive resistors arranged at one or more secondary sensor surfaces which are substantially perpendicular to the rotation axis.

Due to the one or more secondary sensor surfaces being substantially perpendicular to the rotation axis, the secondary force-sensitive resistors may be used to sense forces of a rotatory motion of the shaft around an axis that is perpendicular to the one or more sensor surfaces. The force sensor may therefore be configured to also sense the force on the shaft generated upon a rotatory motion of the shaft around an axis perpendicular to the one or more sensor surfaces.

The secondary force-sensitive resistors may comprise a first group of secondary force-sensitive resistors being oriented perpendicular to a second group of the secondary force-sensitive resistors. The secondary force-sensitive resistors may therefore also be used to sense torsional forces.

According to a further aspect, the present invention is also directed to an electronic dental torque wrench system comprising the electronic dental torque wrench according to the present disclosure, a processing circuit connected to the force sensor and configured to process sensing signal of the force sensor and to output sensing data, and a terminal device, preferably a mobile communication device, with a display unit, the terminal device configured to receive sensing data from the processing circuit and to display the sensing data on the display unit.

Using the processing circuit, the sensing signal of the force sensor can be digitized. The dental practitioner may monitor the torque values the terminal device and therefore receive a precise indication of the applied torque during installation of a dental implant. Due to the terminal device being a separate device, such as a mobile communication device, visual monitoring of the torque values can be facilitated compared to conventional mechanical solutions where the torque values are read from measurement marks on the torque wrench itself. In particular, the dimensions of the electronic dental torque wrench can be made smaller than or kept as small as a mechanical torque wrench used for dental implantology while improving the indication of the torque values.

The digitization of the sensing signal provides the advantage that the sensing data can be used further in various ways, as required. For example, the torque values may be transmitted to another processing unit or stored in a data store. The sensing data may also allow to display the torque values in a browser of the mobile communication device of the dental practitioner.

In some embodiments, the terminal device may comprise an acoustic output unit configured to output an acoustic signal using the sensing data, wherein the acoustic signal concurs with the measured torque values.

Therefore, a dental practitioner may obtain information about the applied torque without having to visually check the torque values on a display.

In some embodiments, the processing circuit is connected to the accelerometer and/or gyroscope sensor and configured to process sensing signal of the accelerometer and/or gyroscope sensor and to output sensing data.

The dental practitioner may therefore also monitor the acceleration/speed/orientation values on the terminal device and therefore receive a precise indication of the operation of the electronic dental torque wrench during installation of a dental implant.

In some embodiments, the electronic dental torque wrench system comprises a data store configured to store sensing data processed by the processing circuit.

Storing the sensing data may be advantageous for digital documentation of the installation process of the dental implant. Furthermore, the stored sensing data may be used for training or demonstration or in case of warranty claims.

In some embodiments, the processing circuit comprises a communication unit configured for wired or wireless sensing data transmission to the terminal device.

In some embodiments, the electronic dental torque wrench system comprises a remote processing system, wherein the communication unit is configured for sensing data transmission to the remote processing system, wherein the terminal device is configured to receive sensing data from the remote processing system.

Transmitting the sensing data to the remote processing system provides the advantage that various terminal devices connected to the remote processing system can receive the sensing data therefrom. This may especially be advantageous for training or demonstration purposes where various users with their terminal devices may access the sensing data of an installation process of a dental implant.

The communication unit may communicate with the remote processing system via a communication network, which may be the internet. The remote processing system may be a cloud-based computer system.

In some embodiments, the processing circuit is configured to receive one or more calibration commands from the terminal device.

Prior to the use of the electronic dental torque wrench, the processing circuit may therefore be used to calibrate at least one of: the force sensor, the accelerometer and/or gyroscope sensor.

According to a further aspect, the present invention is also directed to a method of monitoring an electronic dental torque wrench by an electronic dental torque wrench system according to the present disclosure, comprising the processing circuit executing the steps of: receiving a sensing signal of a torque sensed by the force sensor of the electronic dental torque wrench; processing the sensing signal and outputting sensing data; transmitting the sensing data to the terminal device for display on the display unit.

In some embodiments, the processing circuit executes the steps of: receiving a sensing signal of an acceleration, speed and/or orientation sensed by the accelerometer and/or gyroscope sensor of the electronic dental torque wrench; processing the sensing signal and outputting sensing data; transmitting the sensing data to the terminal device for display on the display unit.

BRIEF DESCRIPTION OF THE DRAWINGS

The present invention will be explained in more detail, by way of exemplary embodiments, with reference to the schematic drawings, in which.

DETAILED DESCRIPTION OF EXEMPLARY EMBODIMENTS

Figure 1A:
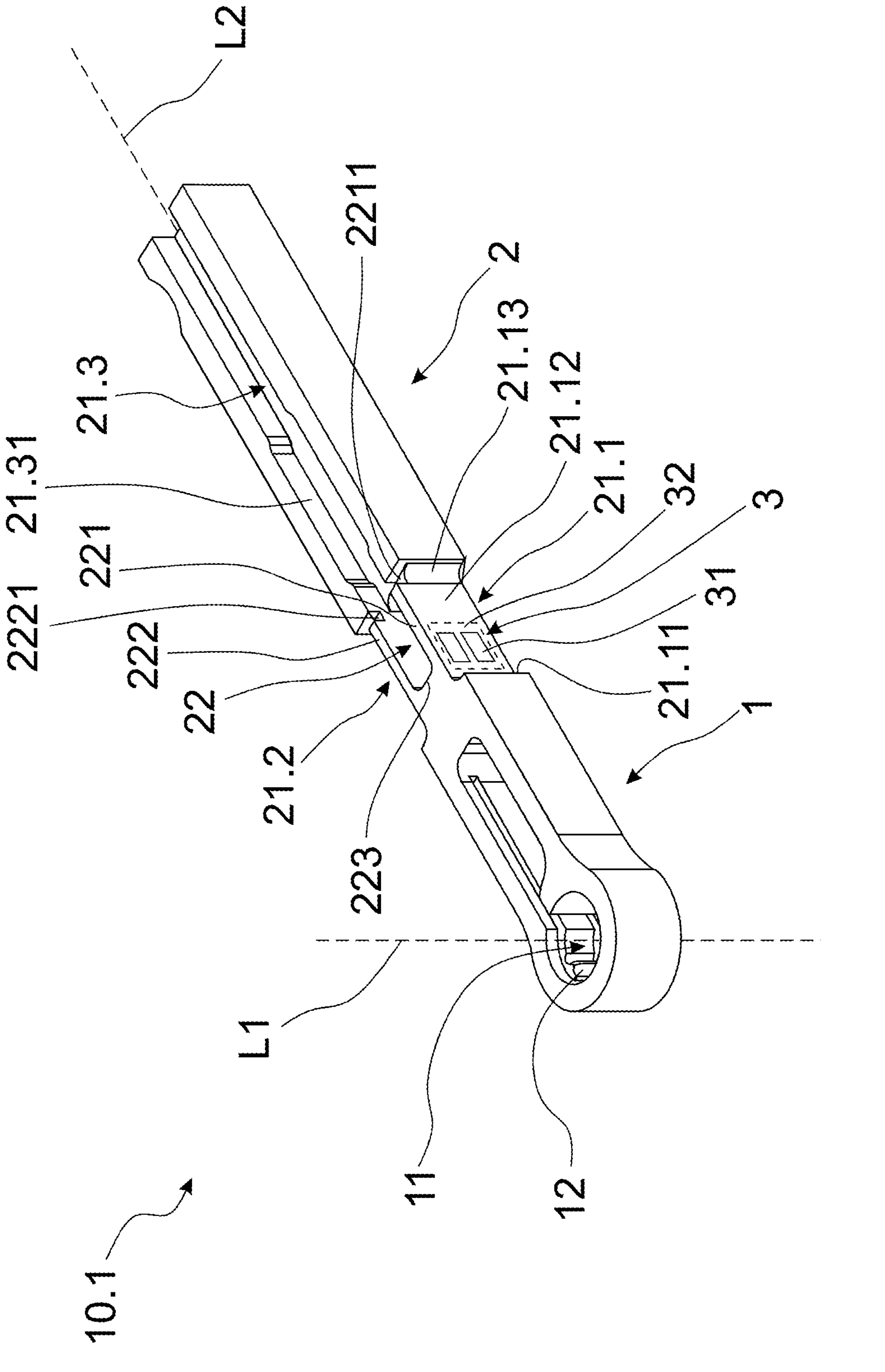
FIG. 1*a* shows a perspective view of an embodiment of an electronic dental torque wrench.

FIG. 1*a* shows a perspective view of an embodiment of an electronic dental torque wrench 10.1 comprising a head 1 and a shaft 2. The head 1 comprises a receiving opening 11 defining a rotation axis L1 and configured to receive a screwing instrument for a dental implant (not shown in FIG. 1). The head 1 further comprises a ratchet 12 configured to engage with the screwing instrument upon rotation f the shaft around the rotation axis L1 in a tightening direction and to provide a freewheel upon rotation of the shaft around the rotation axis L1 against the tightening direction. The shaft 2 comprises force sensor 3 with a plurality of force-sensitive resistors 31 arranged at a first sensor surface 32. In particular, the force sensor 3 may comprise a plurality of strain gauges. The force-sensitive resistors 31 are connected in a Wheatstone bridge circuit. As indicated by a dashed rectangle, the first sensor surface 32 provides a space for the force-sensitive resistors 31 and does not have to be structurally shaped as a separate component. The shaft 2 further comprises a first recess 21.1 and a second recess 21.2 which are mirror-symmetric with respect to the shaft axis L2. The first recess 21.1 comprises a front recess wall 21.11 and a rear recess wall 21.13 which axially delimit a first floor 21.12 of the first recess 21.1. The first sensor surface 32 is arranged at the first floor 21.12, next to the front recess wall 21.11.

A clearance 22 having a shape of a slotted hole is formed within the shaft 2 along the shaft axis L2. In other embodiments, the clearance may have the shape of a borehole, for example having a circular or square shape. The clearance 22 is open in a direction parallel to the rotation axis L1 and closed in and against the tightening direction by a first shaft wall 221 and a second shaft wall 222. The first shaft wall 221 and second shaft wall 222 each comprise an inner surface and an outer surface with respect to the clearance 22. The first sensor surface 32 is arranged at the outer surface of the first shaft wall 221 and at a front end 223 of the clearance 22 with respect to the head 1. The front end 223 of the clearance 22 is axially offset with respect to the front recess wall 21.11 of the first recess 21.1 such that a part of the first floor 21.12 of the first recess 21.1 coincides with the outer surface of the first shaft wall 221. The axial offset of the clearance 22 is shaped such that the front end 223 of the clearance 22 is axially positioned between the front recess wall 21.11 and the rear recess wall 21.13 of the first recess 21.1, whereby the front end 223 of the clearance 22 is closer to the front recess wall 21.11 than to the rear recess wall 21.13 of the first recess 21.1. Thus, the force-sensitive resistors 31 are positioned where the maximal strain at the first recess 21.1 occurs due to the axial offset of the clearance 22. Similarly, force-sensitive resistors may be arranged at the second recess 21.2 in a mirror-symmetric fashion with respect to the shaft axis L2.

The shaft 2 further comprises a third recess 21.3 which is arranged in a plane perpendicular to the rotation axis L1 and perpendicularly to the first and second recesses 21.1, 21.2. In other embodiments, the third recess may be arranged at different orientations with respect to the rotation axis L1. The third recess 21.3 extends from the clearance 22 through the rear region of the shaft 2 and is dimensioned to receive one or more wires for electrically contacting the force-sensitive resistors 31. The third recess 21.3 comprises an enlarged section 21.31 where additional components of the force sensor 3, such as temperature compensation elements, may be arranged.

The first shaft wall 221 comprises a first notch 2211 which extends perpendicular to the outer surface of the first shaft wall 221. The first notch 2211 provides a passage from the outer surface of the first shaft wall 221 to the third recess 21.3 such that wires can be guided from the force-sensitive resistors 31 along the outer surface of the first shaft wall 221, through the notch 2211 to the third recess 21.3. The second shaft wall 222 comprises a second notch 2221 which may be used as a passage for wires contacting force-sensitive resistors which may be arranged at an outer surface of the second shaft wall 222.

The force sensor 3 comprises a plurality of temperature compensation elements (not shown in FIG. 1*a*) configured to compensate a temperature drift of the sensing signal of the force sensor 3. Different temperature dependencies of the force-sensitive resistors 31 are at least partially compensated by additional compensation resistors, which may comprise or consist of additional wire portions soldered into source and drain parts to the force-sensitive resistors 31. The temperature compensation elements may be arranged in the first recess 21.1, the second recess 21.2 and/or the third recess 21.3.

Figure 1B:
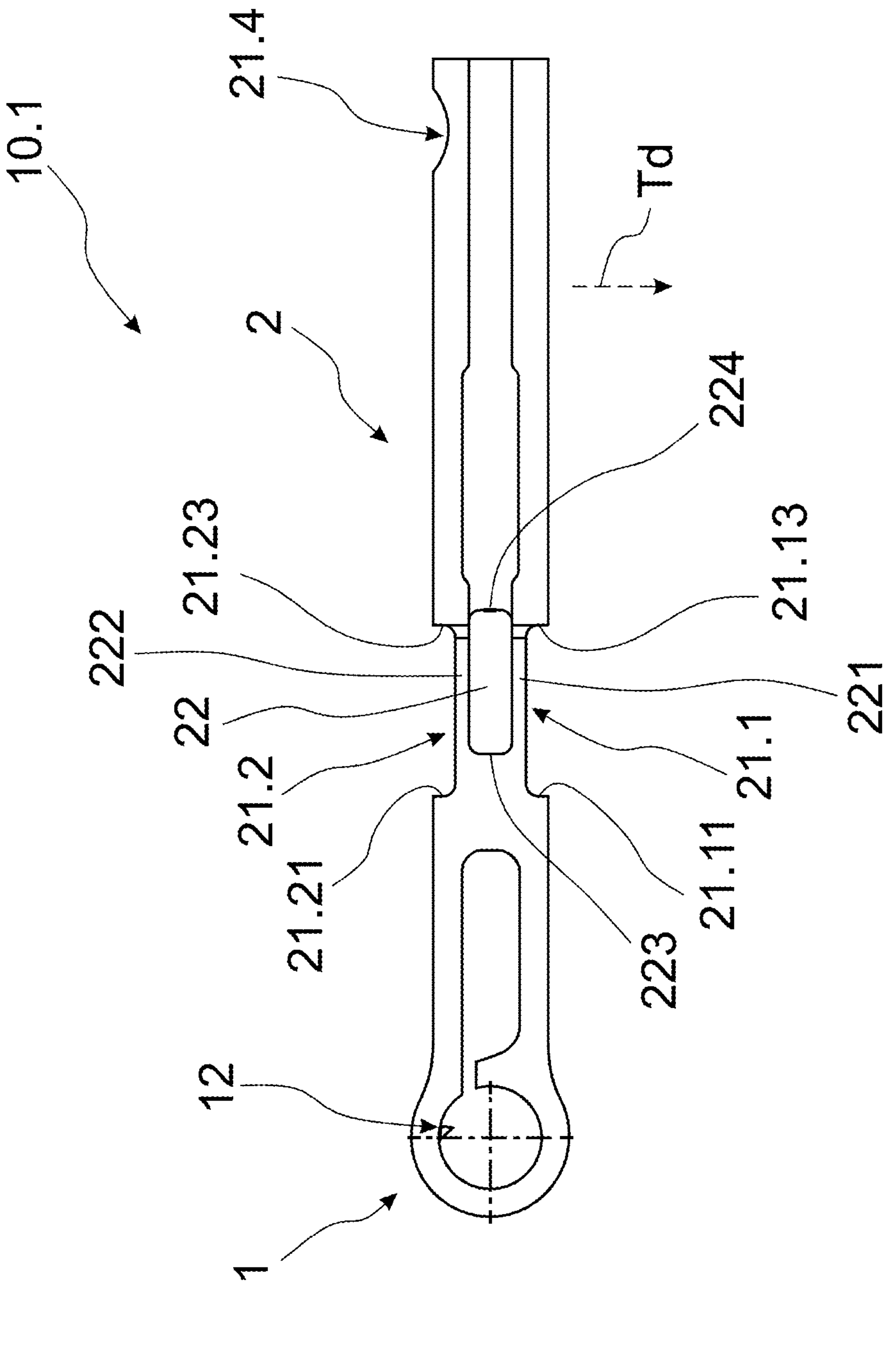
FIG. 1*b* shows a top view of the electronic dental torque wrench of FIG. 1*a;*

FIG. 1*b* shows a top view of the electronic dental torque wrench 10.1 of FIG. 1*a*. It can be recognized that the clearance 22 is axially offset in a fashion that the rear recess wall 21.13 of the first recess 21.1 is closer to the head 1 than the rear end 224 of the clearance 22. Due to the mirror-symmetric arrangement of the first recess 21.1 and the second recess 21.2, the rear recess wall 21.23 of the second recess 21.2 is accordingly also closer to the head 1 that the rear end 224 of the clearance 22. The rear end 224 of the clearance 22 therefore extends further into the rear region of the shaft 2 than the first recess 21.1. The maximal strain predominantly occurs at the front end 223 of the clearance 22 where the first shaft wall 221 and second shaft wall 222 join the solid or, respectively, filled portion of the shaft 2. Due to the axial offset of the clearance 22, the position where the maximal strain occurs is located at a front region of the first recess 21.1 and at a front region of the second recess 21.2. Both the front recess wall 21.11 of the first recess 21.1 and the front recess wall 21.21 of the second recess 21.2 are closer to the head 1 than the front end 223 of the clearance 22. The shaft 2 comprises a fourth recess 21.4 configured to engage with a protective sleeve (not shown in FIG. 1*b*) in a snap-fit fashion. The tightening direction Td, in which the ratchet 12 engages with the screwing instrument and against which the ratchet 12 provides a freewheel, is indicated in FIG. 1*b*.

Figure 2:
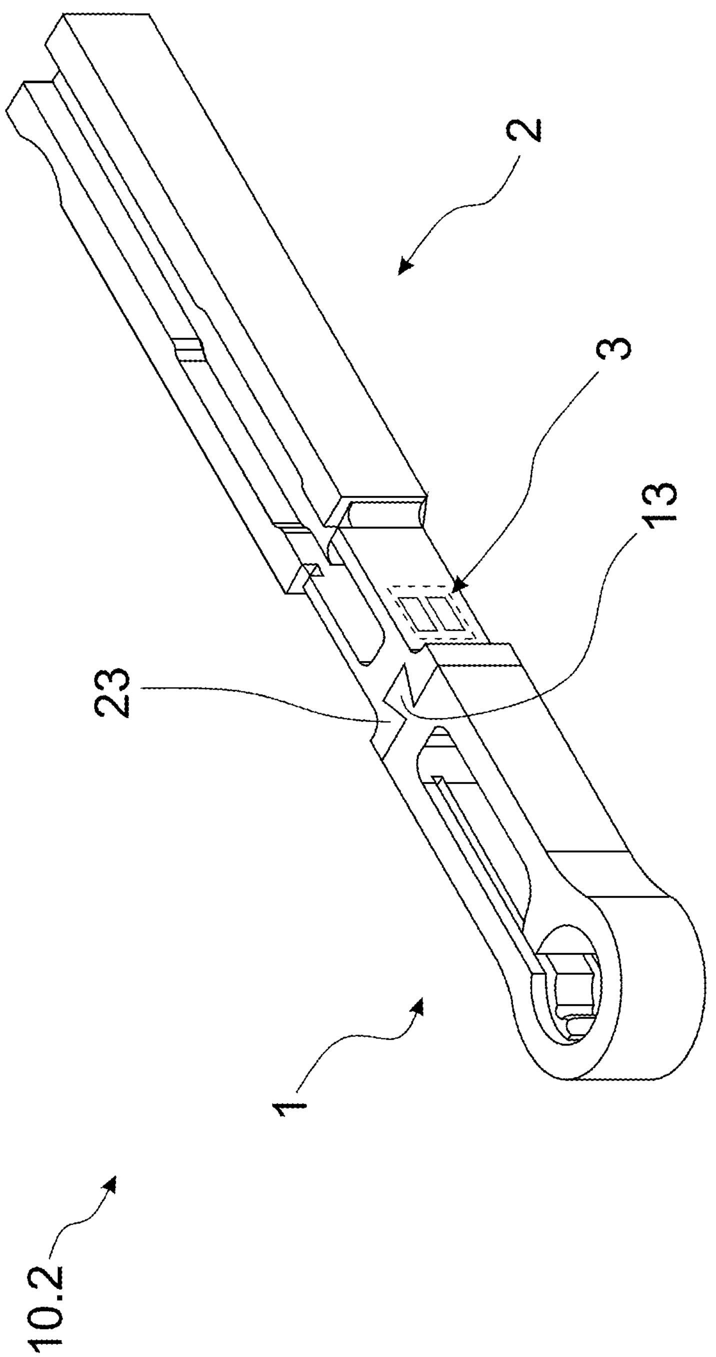
FIG. 2 shows a perspective view of an embodiment of an electronic dental torque wrench with a releasably connected head and shaft.

FIG. 2 shows a perspective view of an embodiment of an electronic dental torque wrench 10.2. The head 1 comprises a first interface connector 13 and the shaft 2 comprises a second interface connector 23. The head 1 and the shaft 2 are releasably interconnected by the first interface connector 13 and the second interface connector 23 forming a dovetail connection. For sterilization, the head 1 can be separated from the shaft 2, such that the force sensor 3 is not damaged by the sterilization process. Besides the two-part configuration with releasably connectable head 1 and shaft 2, the electronic dental torque wrench 10.2 corresponds to the electronic dental torque wrench 10.1 shown in FIG. 1*a* and FIG. 1*b*, in particular with regard to the force sensor, first, second and third recesses and the clearance.

Figure 3:
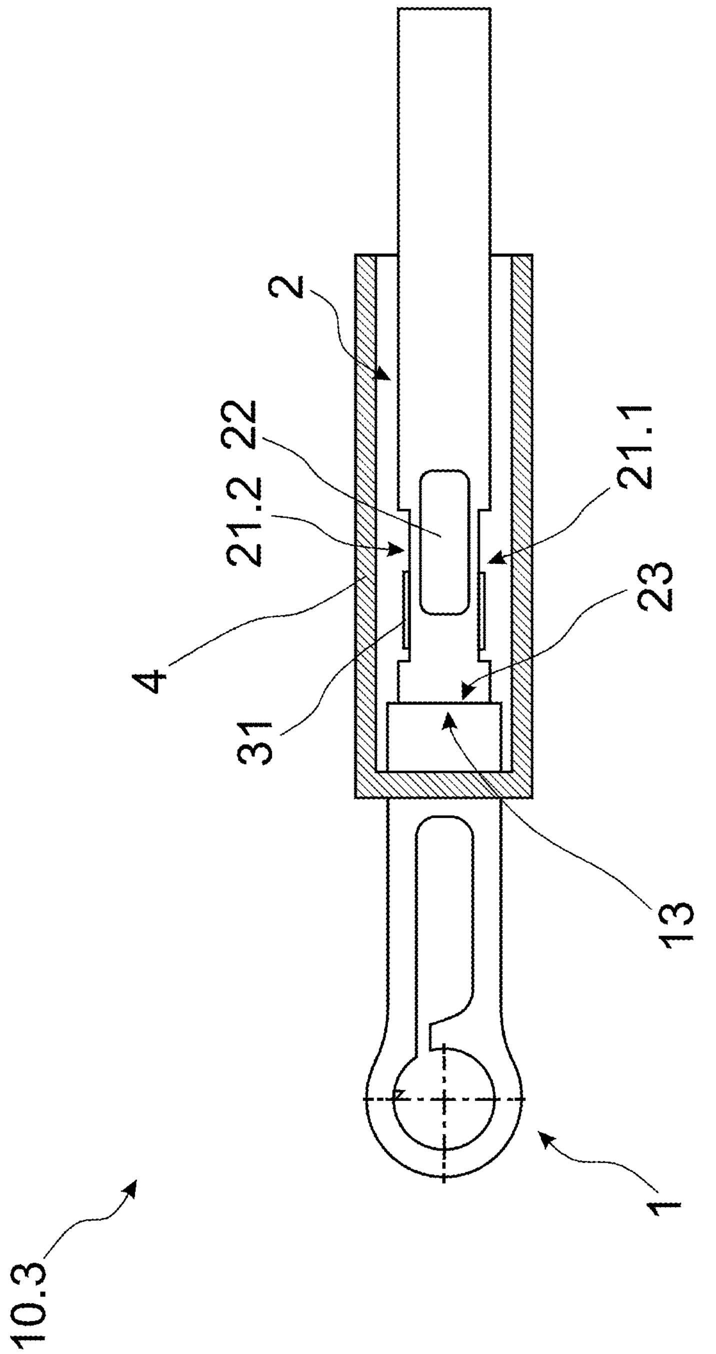
FIG. 3 shows a top view of an embodiment of an electronic dental torque wrench with a protective sleeve.

FIG. 3 shows an embodiment of an electronic dental torque wrench 10.3 with a head 1 and a shaft 2 which are releasably connected to each other. The head 1 comprises a first interface connector 13 with a socket and the shaft 2 comprises a second interface connector 23 with a plug, forming together a plug-socket connection. A protective sleeve 4 is placed over the first recess 21.1 and the second recess 21.2 such that the force-sensitive resistors 31 placed therein are protected. The protective sleeve extends from a rear portion of the head 1 to a rear portion of the shaft 2 which protrudes out of the protective sleeve 4. In some embodiments, the protective sleeve 4 may also cover the whole shaft 2. In FIG. 3, the protective sleeve 4 is open at the rear side and closed at the front side facing the head 1 apart from an aperture for receiving the rear portion of the head 1. In some embodiments, the protective sleeve 4 may be closed also at the rear side apart from an aperture for receiving the shaft 2. The protective sleeve 4 may additionally comprise at least one feedthrough for wires connected the force-sensitive resistors arranged within the protective sleeve 4. The protective sleeve 4 may be fixedly mounted to the head 1 or connected to the head 1 before the shaft 2 is introduced into the protective sleeve 4 and connected with the head 1. Alternatively, especially for an embodiment with a closed rear side of the protective sleeve 4, the protective sleeve 4 may be fixedly mounted to the shaft 2 or connected to the shaft 2 before the rear portion of the head 1 is introduced into the protective sleeve 4. In the shown embodiment of FIG. 3, the protective sleeve 4 is made of a plastic.

Figure 4:
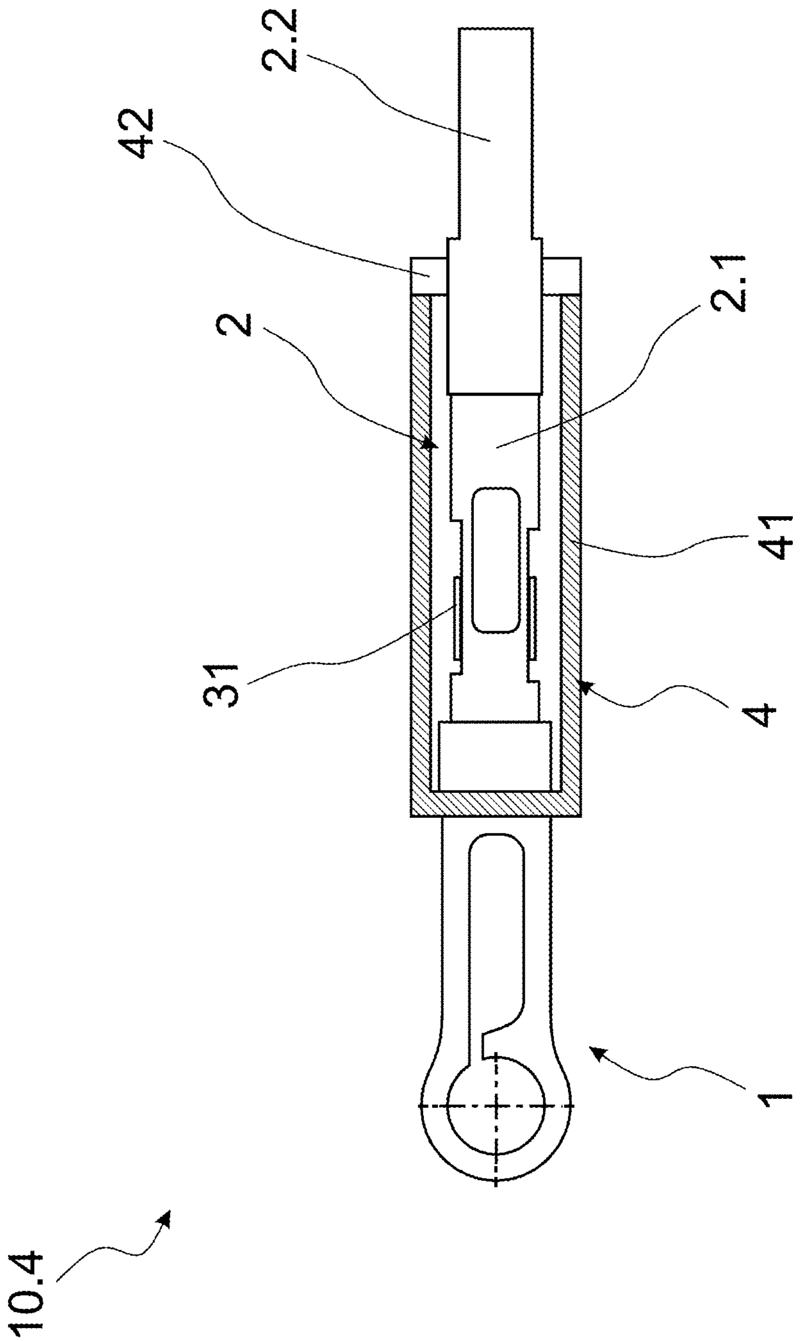
FIG. 4 shows a top view of an embodiment of an electronic torque wrench with a protective sleeve.

FIG. 4 shows an embodiment of an electronic dental torque wrench 10.4 with a head 1 and a shaft 2 which are releasably connected to each other by a plug-socket connection. The shaft 2 comprises a sensor-carrying part 2.1 and a gripping part 2.2 which are releasably mounted together by a plug-socket connection. The protective sleeve 4 comprises a main body 41 and a cap 42 which closes the rear end of the main body 41. The cap 42 comprises a central aperture designed to receive the gripping part 2.2 therethrough. Wires which contact the force-sensitive sensors 31 may be guided through wire channels formed on or at least partially within the gripping part 2.2. The head 1 and the gripping part 2.2 may be disconnected from the sensor-carrying part 2.1 for sterilization. The main body 41 and the cap 42 may also be sterilized before or after use of the electronic dental torque wrench 10.4. The electronic dental torque wrench 10.4 has therefore the advantage that the parts which may come into contact with the patient may be sterilized while the sensor-carrying part 2.1 with the force-sensitive resistors 31 are not required to undergo sterilization which may be detrimental to the electronic components of the force sensor.

Figure 5A:
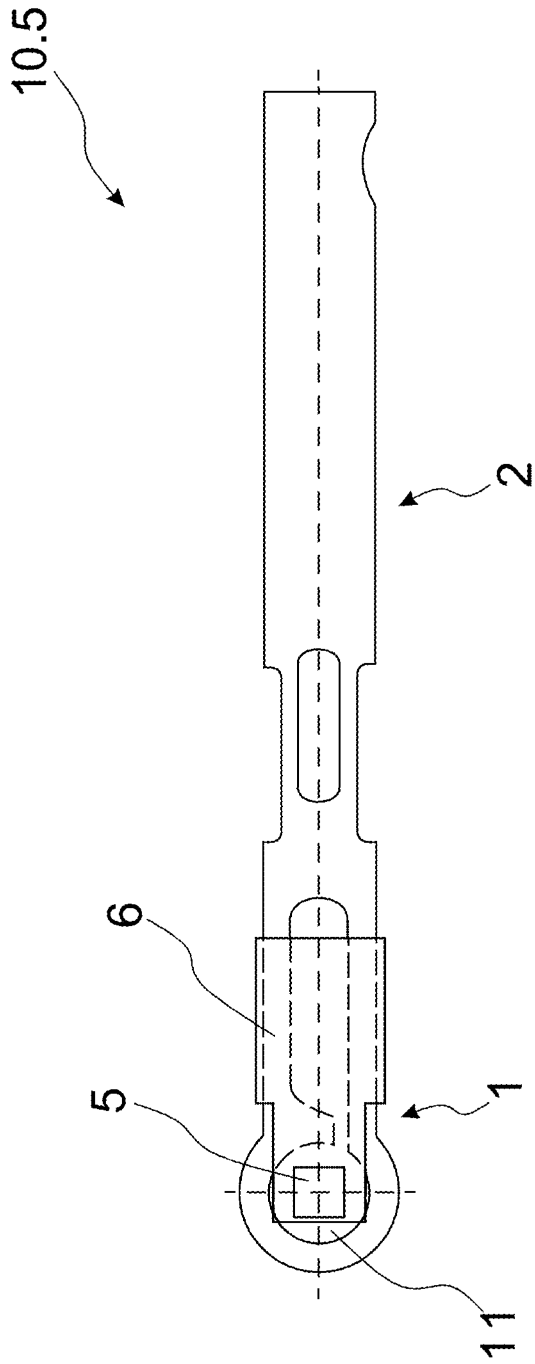
FIG. 5*a* shows a top view of an embodiment of an electronic dental torque wrench with an acceleration-gyroscope sensor arranged at the receiving opening of the head and on the rotation axis of the receiving opening.
Figure 5B:
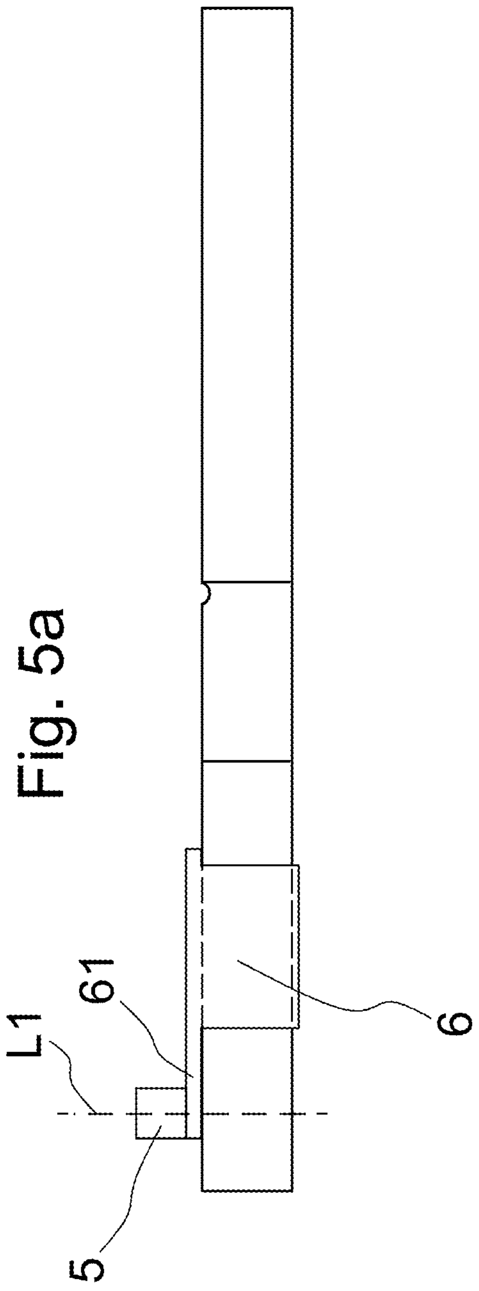
FIG. 5*b* shows a side view of the embodiment of the electronic dental torque wrench of FIG. 5*a;*

FIGS. 5*a* and 5*b* show a top view and a side view of an embodiment of an electronic dental torque wrench 10.5 comprising a combined acceleration-gyroscope sensor 5. The acceleration-gyroscope sensor 5 is arranged on a positioning sleeve 6 which is placed over the head 1 of the electronic dental torque wrench 10.5. The positioning sleeve 6 comprises a cantilevered carrier 61 on which the acceleration-gyroscope sensor 5. The positioning sleeve 6 is dimensioned such that the acceleration-gyroscope sensor 5 is positioned at the receiving opening 11 of the head 1 and on the rotation axis L1. Complex calculation for transforming the raw signal is therefore not required when processing the sensor data. The positioning sleeve 6 is configured that the acceleration-gyroscope sensor 5 can be positioned on either side of the receiving opening 11 (i.e. on the upper side of the receiving opening 11 or on the underside of the receiving opening 11, as shown in FIG. 5), depending on whether the electronic dental torque wrench 10.5 is used for torquing in clockwise or counterclockwise direction.

Figures 6A, 6B:
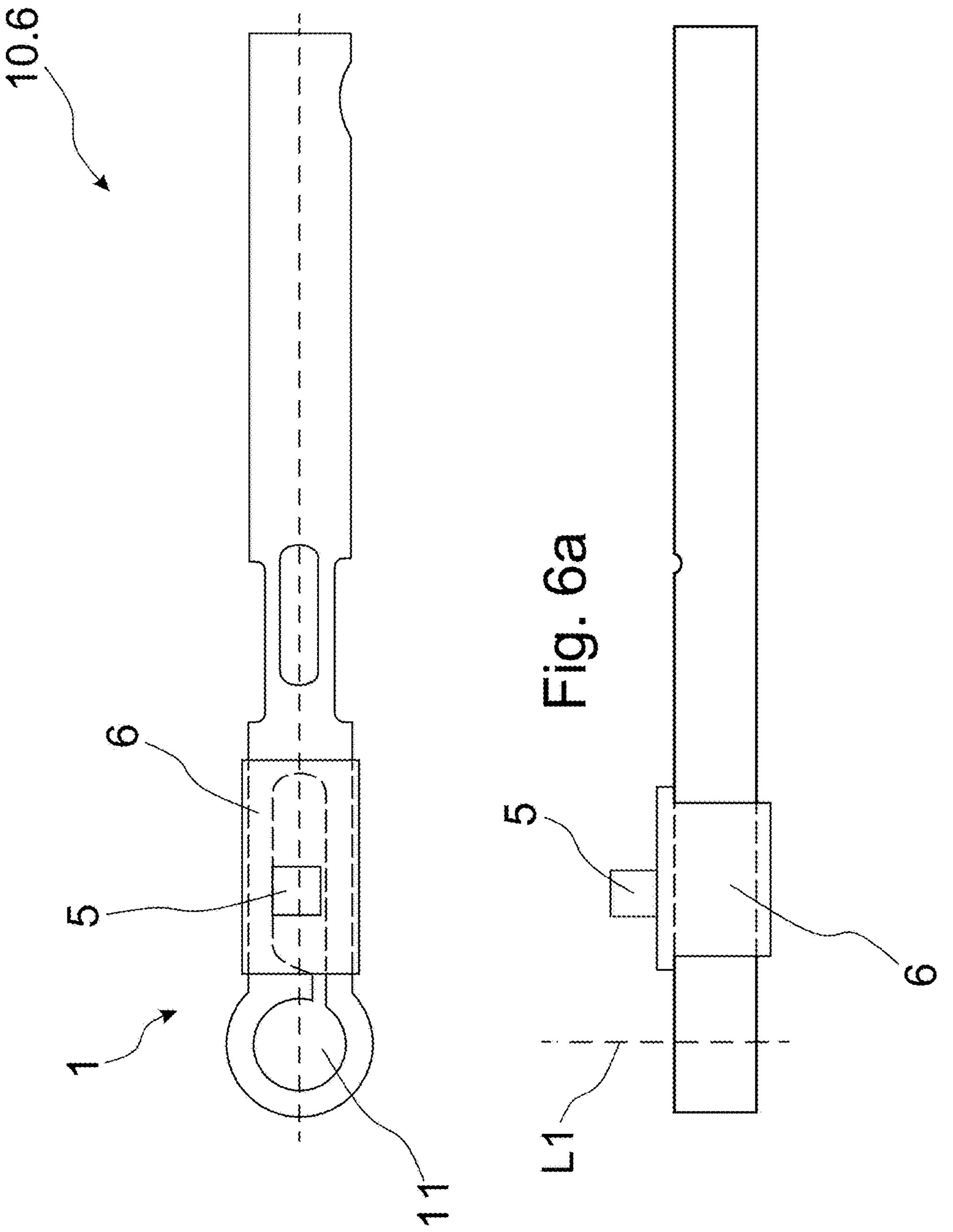
FIG. 6*a* shows a top view of an embodiment of an electronic dental torque wrench with an acceleration-gyroscope sensor arranged at the receiving opening of the head and offset to the rotation axis of the receiving opening.
FIG. 6*b* shows a side view of the embodiment of the electronic dental torque wrench of FIG. 6*a;*

FIGS. 6*a* and 6*b* show a top view and a side view of an embodiment of an electronic dental torque wrench 10.6 comprising a combined acceleration-gyroscope sensor 5 which is arranged on a positioning sleeve 6. The positioning sleeve 6 is placed over the head 1 of the electronic dental torque wrench 10.6. Different to the embodiment as shown in FIG. 5, however, the positioning sleeve 6 is configured that the acceleration-gyroscope sensor 5 is placed offset to the receiving opening 11 and the rotation axis L1. The positioning sleeve 6 and the acceleration-gyroscope sensor 5 can fixedly be positioned, independent of whether the electronic dental torque wrench 10.6 is used for torquing in clockwise or counterclockwise direction.

Figure 7A:
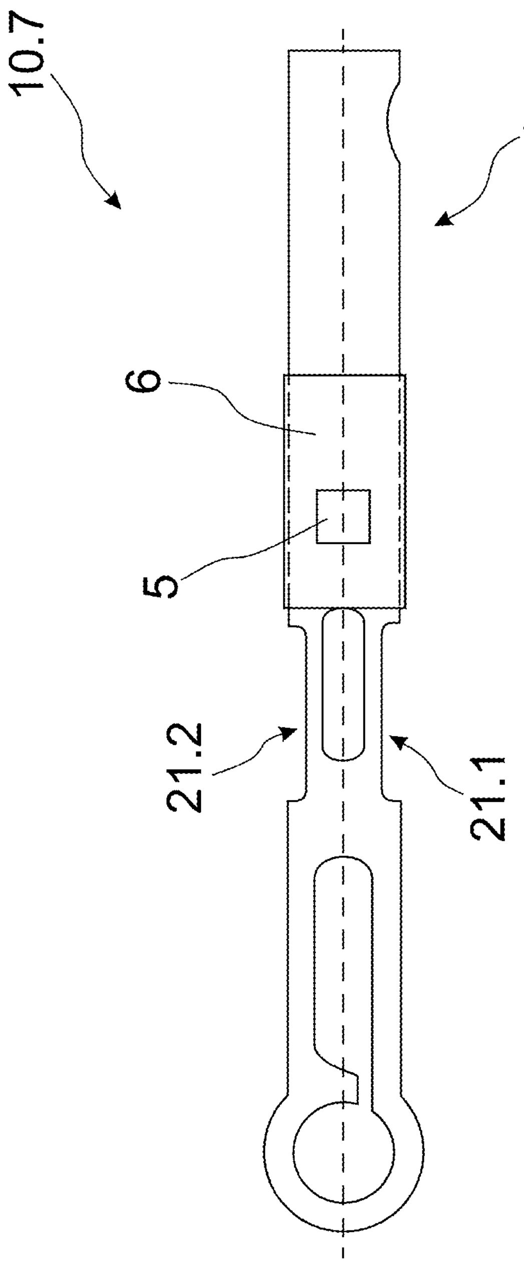
FIG. 7*a* shows a top view of an embodiment of an electronic dental torque wrench with an acceleration-gyroscope sensor arranged at the shaft.
Figure 7B:
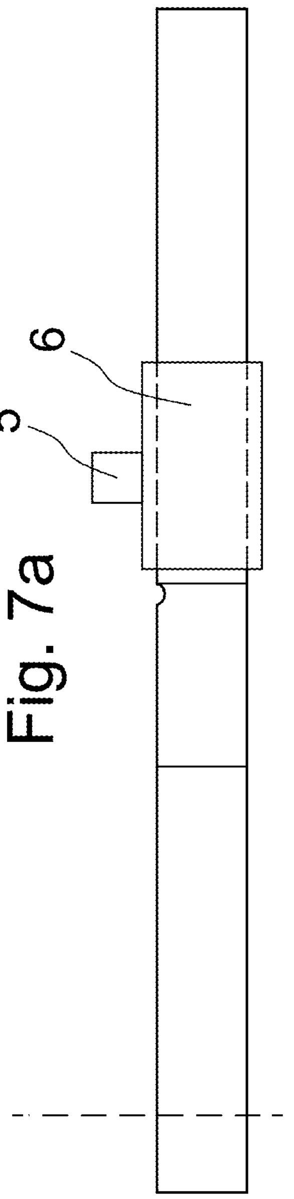
FIG. 7*b* shows a side view of the embodiment of the electronic dental torque wrench of FIG. 7*a;*

FIGS. 7*a* and 7*b* show a top view and a side view of an embodiment of an electronic dental torque wrench 10.7 comprising a combined acceleration-gyroscope sensor 5 arranged on the shaft 2 of the electronic dental torque wrench 10.7. The acceleration-gyroscope sensor 5 is arranged on a positioning sleeve 6 which is placed over the shaft 2. The positioning sleeve 6 and the acceleration-gyroscope sensor 5 can fixedly be positioned, independent of whether the electronic dental torque wrench 10.6 is used for torquing in clockwise or counterclockwise direction. The positioning sleeve 6 is positioned offset to the first and second recesses 21.1, 21.2.

In some embodiments, the positioning sleeve 6 may be placed over the first and second recesses 21.1, 21.2 and therefore function at the same time as a protective sleeve for force-sensitive resistors arranged in the first and/or second recesses 21.1, 21.2.

Figure 8A:
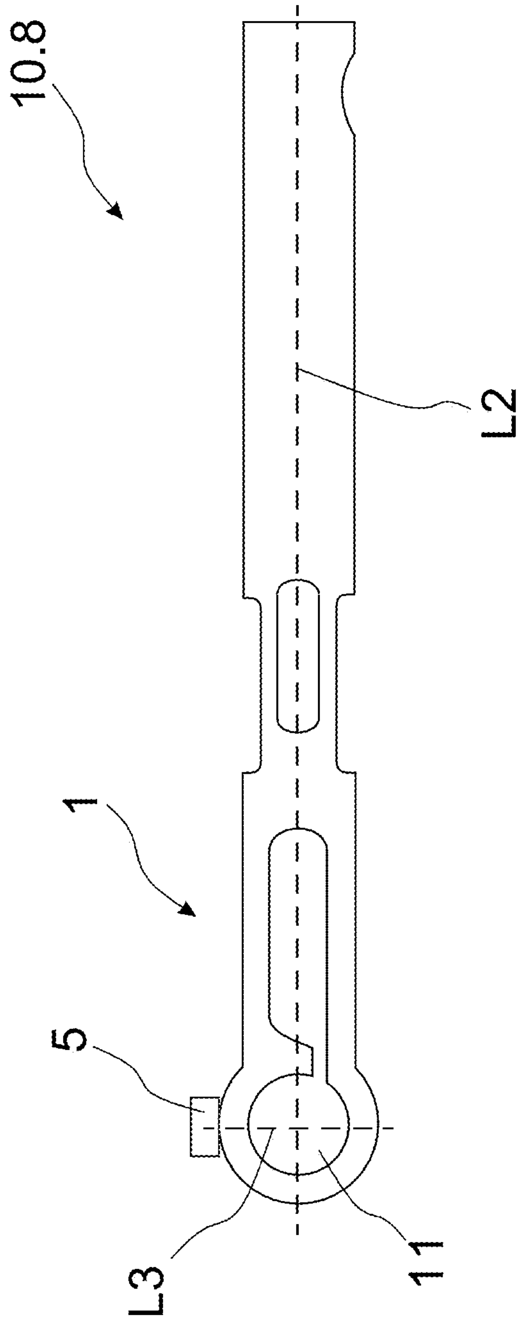
FIG. 8*a* shows a top view of an embodiment of an electronic dental torque wrench with an acceleration-gyroscope sensor arranged at the receiving opening.

FIG. 8*a* shows a top view of an embodiment of an electronic dental torque wrench 10.8 with a combined acceleration-gyroscope sensor 5 arranged at the receiving opening 11 of the head 1, but offset to the rotation axis of the receiving opening 11. Instead, the acceleration-gyroscope sensor 5 is arranged on an axis L3 which is perpendicular to the shaft axis L2 and perpendicular to the rotation axis of the receiving opening 11.

Figure 8B:
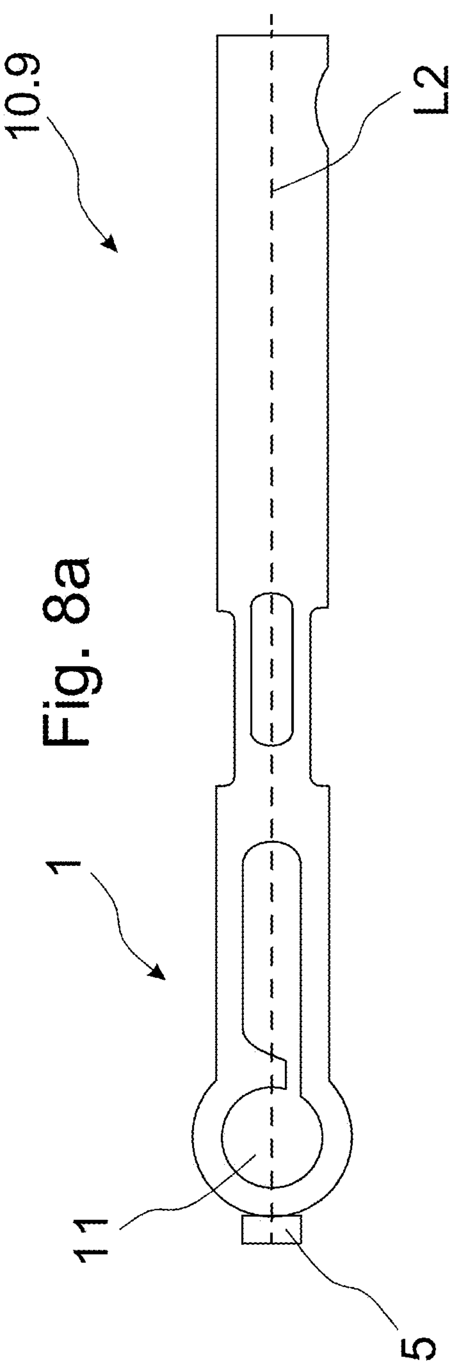
FIG. 8*b* shows a top view of an embodiment of an electronic dental torque wrench with an acceleration-gyroscope sensor arranged at the receiving opening.

FIG. 8*b* shows a top view of a further embodiment of an electronic dental torque wrench 10.9 with a combined acceleration-gyroscope sensor 5 arranged at the receiving opening 11 of the head 1, but also offset to the rotation axis of the receiving opening 11. Different to the embodiment as shown in FIG. 8*a*, however, the acceleration-gyroscope sensor 5 is arranged on the shaft axis L2.

Figure 9:
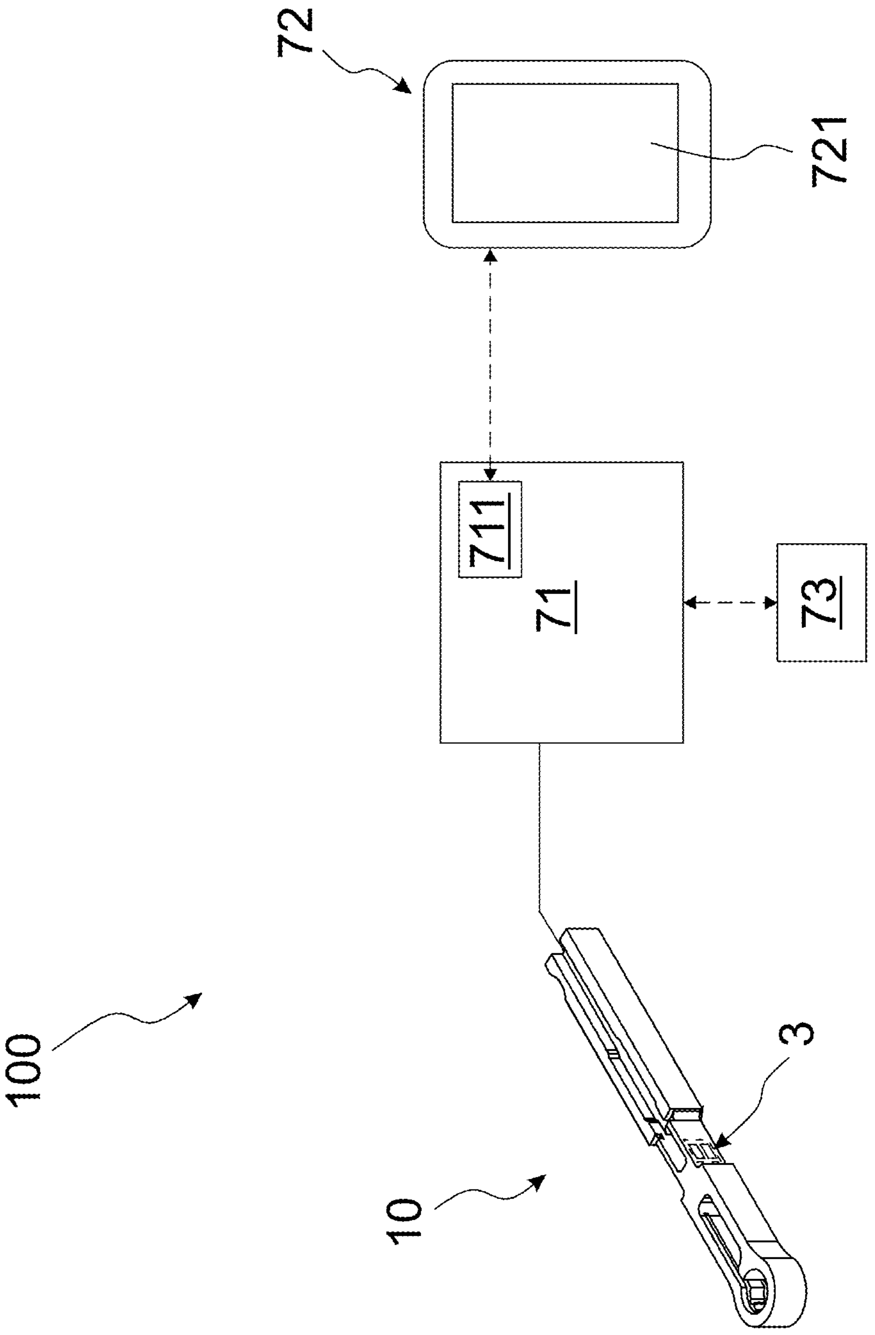
FIG. 9 shows an embodiment of an electronic dental torque wrench system.

FIG. 9 shows an embodiment of an electronic dental torque wrench system 100 comprising an electronic dental torque wrench 10, a processing circuit 71 connected to the force sensor 3 of the electronic dental torque wrench 10 and a terminal device 72 embodied as a mobile communication device connected to the processing circuit 71. The processing circuit 71 processes the sensing signal of the force sensor 3 and outputs sensing data to the terminal device 72. The terminal device 72 receives the sensing data from the processing circuit 71 and displays the sensing data on the display unit 721 of the terminal device 72. The electronic dental torque wrench system 100 comprises a data store 73 configured to store the sensing data processed by the processing circuit 71. The processing circuit 71 comprises a communication unit 711 configured for wireless communication with the terminal device 72 by which the sensing data can be transmitted. The processing circuit 71 is configured to receive one or more calibration commands from the terminal device 72 in order to calibrate the torque range to be sensed by the force sensor 3.

Figure 10:
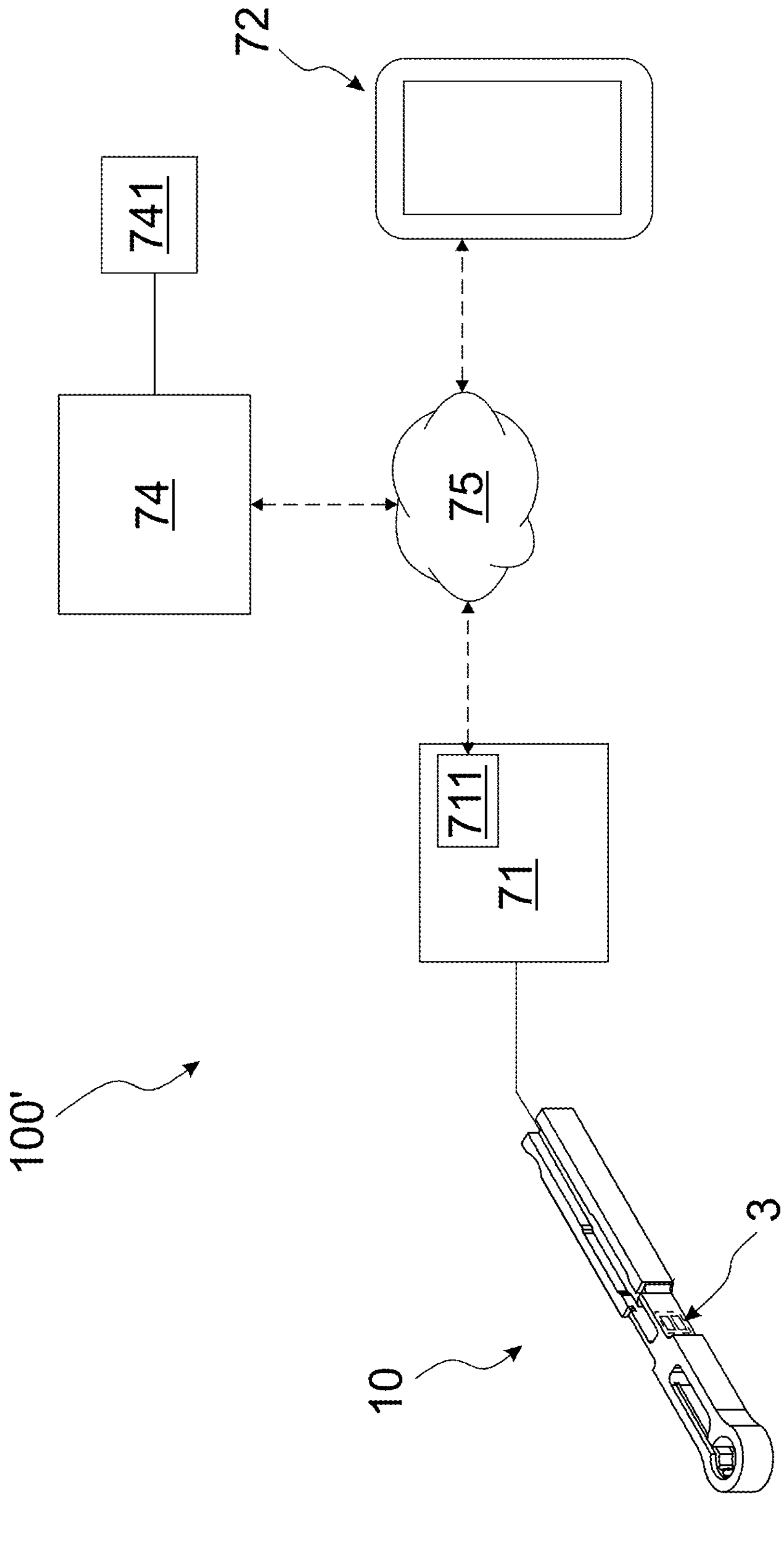
FIG. 10 shows an embodiment of an electronic dental torque wrench system.

FIG. 10 shows an embodiment of an electronic dental torque wrench system 100' comprising an electronic dental torque wrench 10 with a force sensor 3 similar to the electronic dental torque wrench system 100 as shown in FIG. 9. The electronic dental torque wrench system 100' comprises a remote processing system 74, especially a cloud-based computer system, which communicates with the communication unit 711 of the processing circuit 71 via a communication network 75, which may be the internet. Sensing data as processed by the processing circuit 71 is transmitted to the remote processing system 74 via the communication network 75. The remote processing system 74 comprises a data store 741 where the sensing data received from the processing circuit 71 can be stored. The terminal device 72 can in turn receive the sensing data from the remote processing system 74 via the communication network 75. A user of the electronic dental torque system 100' may input one or more calibration commands at the terminal device 72 which are transmitted to the remote processing system 74 via the communication network 75. The remote processing system may process the one or more calibration commands and transmit those to the processing circuit 71 via the communication network 75.

Figure 11:
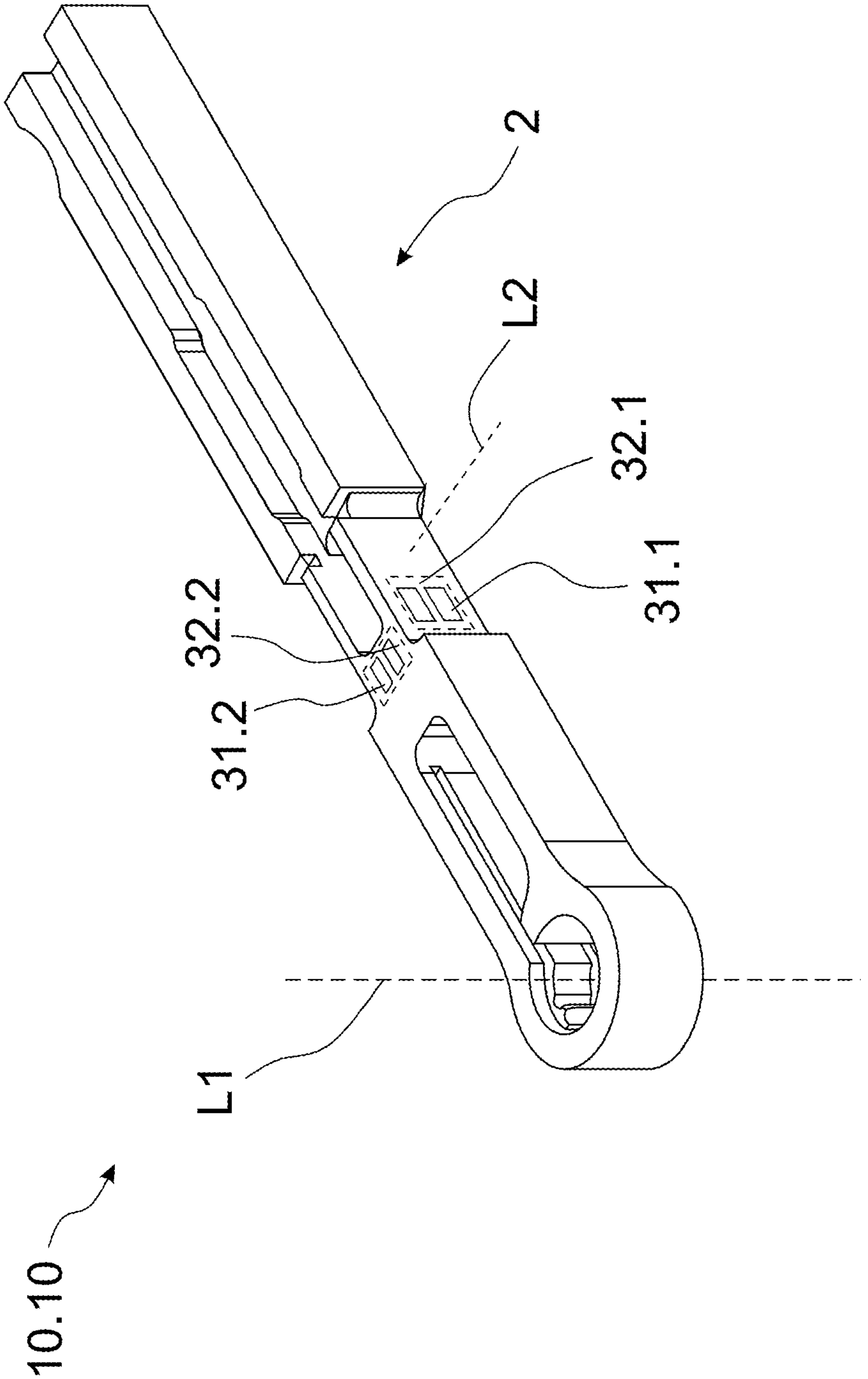
FIG. 11 shows a perspective view of an embodiment of an electronic dental torque wrench.

FIG. 11 shows a perspective view of an embodiment of an electronic dental torque wrench 10.10 with a plurality of force-sensitive resistors 31.1 arranged at a sensor surface 32.1. The electronic dental torque wrench 10.10 further comprises a plurality of secondary force-sensitive resistors 31.2 arranged at a secondary sensor surface 32.2 that is perpendicularly oriented to the rotation axis L1 and to the sensor surface 32.1. The secondary force-sensitive resistors 31.2 may be used by the force sensor to sense forces generated upon a rotatory motion of the shaft 2 around an axis L2 perpendicular to the sensor surface 32.1. The force sensor of the electronic dental torque wrench 10.10 with the force-sensitive resistors 31.1 and the secondary force-sensitive resistors 31.2 may therefore be configured to sense forces upon rotation of the saft around the rotation axis L1 and around the axis L2.

Figure 12:
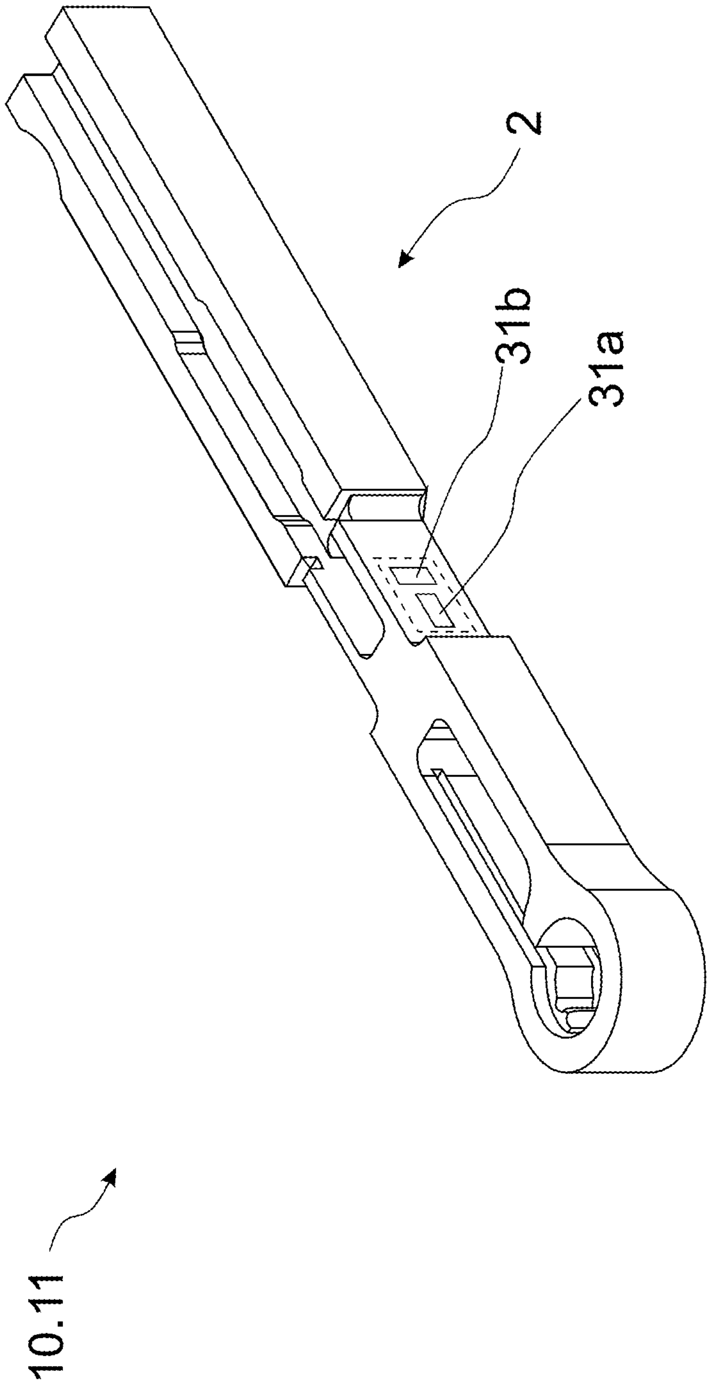
FIG. 12 shows a perspective view of an embodiment of an electronic dental torque wrench.

FIG. 12 shows a perspective view of an embodiment of an electronic dental torque wrench 10.11. The force sensor 3 comprises a first group of force-sensitive resistors 31*a* oriented perpendicularly oriented to a second group of force-sensitive resistors 31*b*. The force sensor 3 may therefore also be configured to sense torsional forces acting on the shaft 2.

The invention claimed is:

1. An electronic dental torque wrench, comprising a head with a receiving opening defining a rotation axis and configured to receive a screwing instrument, a shaft defining a shaft axis and configured for applying a torque to the head, wherein the receiving opening is configured to engage with the screwing instrument upon rotation of the shaft around the rotation axis in a tightening direction, wherein the shaft comprises a force sensor comprising one or more force-sensitive resistors and configured to sense the force on the shaft generated upon rotation of the shaft around the rotation axis in a tightening direction, wherein the one or more force-sensitive resistors are arranged at one or more sensor surfaces which are substantially perpendicular to the tightening direction, wherein the shaft comprises a clearance which is open in a direction parallel to the rotation axis and closed in and against the tightening direction by a first shaft wall and a second shaft wall each having an outer surface and an inner surface, wherein the one or more sensor surfaces are arranged at the shaft walls.

2. The electronic dental torque wrench according to claim 1, wherein the head comprises a ratchet arranged at the receiving opening, wherein the ratchet is configured to engage with the screwing instrument upon rotation of the shaft around the rotation axis in a tightening direction and to provide a freewheel upon rotation of the shaft around the rotation axis against the tightening direction.

3. The electronic dental torque wrench according to claim 1, wherein the one or more sensor surfaces are arranged at a front end and/or at a rear end of the clearance with respect to the head of the electronic dental torque wrench.

4. The electronic dental torque wrench according to claim 1, wherein the one or more sensor surfaces are arranged at the outer surface of the first shaft wall and/or the second shaft wall, or wherein the one or more sensor surfaces are arranged at the inner surface of the first shaft wall and/or the second shaft wall.

5. The electronic dental torque wrench according to claim 1, wherein one or more of the one or more sensor surfaces are arranged at the outer surface of the first shaft wall and/or the second shaft wall and one or more of the one or more sensor surfaces are arranged at the inner surface of the first shaft wall and/or the second shaft wall.

6. The electronic dental torque wrench according to claim 1, wherein the clearance has a shape of a slotted hole.

7. The electronic dental torque wrench according to claim 1, wherein the shaft comprises one or more recesses, each having a floor which is delimited by a front and a rear recess wall with respect to the shaft axis, wherein a sensor surface of the one or more sensor surfaces is arranged at the floor, wherein a front end of the clearance is axially offset with respect to the front recess wall of the one or more recesses such that the front end of the clearance is axially positioned between the front recess wall and the rear recess wall of each of the one or more recesses.

8. The electronic dental torque wrench according to claim 7, wherein the axial position of the front end of the clearance is closer to the front recess wall than to the rear recess wall of each of the one or more recesses or wherein the axial position of the front end of the clearance is closer to the rear recess wall than to the front recess wall of each of the one or more recesses.

9. The electronic dental torque wrench according to claim 7, wherein the rear recess wall of each of the one or more recesses is closer to the head than a rear end of the clearance, or wherein a rear end of the clearance is axially offset with respect to the rear recess wall of each of the one or more recesses such that the rear end of the clearance is axially positioned between the front recess wall and the rear recess wall of each of the one or more recess.

10. The electronic dental torque wrench according to claim 1, wherein the shaft comprises a third recess, extending along the shaft axis, wherein the third recess extends from the clearance.

11. The electronic dental torque wrench according to claim 1, wherein the head comprises a first interface connector and the shaft comprises a second interface connector interconnectable with the first interface connector such that the head and the shaft are releasably connectable by an interface formed by the first interface connector and the second interface connector, wherein the first interface connector and the second interface connector are configured to form a form-fit and/or force-fit connection.

12. The electronic dental torque wrench according to claim 1, wherein the force sensor comprises one or more temperature compensation elements configured to compensate a temperature drift of a sensing signal of the force sensor.

13. The electronic dental torque wrench according to claim 1, comprising an accelerometer and/or a gyroscope sensor, wherein the accelerometer and/or gyroscope sensor is arranged at the head.

14. The electronic dental torque wrench according to claim 13, comprising a positioning sleeve placeable over a portion of the electronic dental torque wrench, wherein the accelerometer and/or gyroscope sensor is arranged on the positioning sleeve.

15. The electronic dental torque wrench according to claim 14, wherein the positioning sleeve is placeable over the head, or wherein the positioning sleeve is placeable over the shaft.

16. The electronic dental torque wrench according to claim 1, comprising a protective sleeve placeable over at least a part of the force sensor.

17. The electronic dental torque wrench according to claim 1, wherein the force sensor comprises one or more secondary force-sensitive resistors arranged at one or more secondary sensor surfaces which are substantially perpendicular to the rotation axis.

18. An electronic dental torque wrench system comprising the electronic dental torque wrench according to claim 1, a processing circuit connected to the force sensor and configured to process sensing signal of the force sensor and to output sensing data, and a terminal device, with a display unit, the terminal device configured to receive sensing data from the processing circuit and to display the sensing data on the display unit.

19. The electronic dental torque wrench system according to claim 18, wherein the processing circuit comprises a communication unit configured for wired or wireless sensing data transmission to the terminal device, the electronic dental torque wrench system comprising a remote processing system, wherein the communication unit is configured for sensing data transmission to the remote processing system, wherein the terminal device is configured to receive sensing data from the remote processing system.

20. The electronic dental torque wrench system according to claim 18, wherein the processing circuit is configured to receive one or more calibration commands from the terminal device.

* * * * *